US012667552B2

(12) United States Patent
Forbes-Blom et al.

(10) Patent No.: US 12,667,552 B2
(45) **Date of Patent: *Jun. 30, 2026**

(54) DIETARY BUTYRATE

(71) Applicant: SOCIETE DES PRODUITS NESTLE S.A., Vevey (CH)

(72) Inventors: Elizabeth Forbes-Blom, Epalinges (CH); Martinas Kuslys, Grosshoechstetten (CH); Ralf Heine, Berlin (DE); Amaury Patin, Lausanne (CH)

(73) Assignee: Societe des Produits Nestle S.A., Vevey (CH)

( * ) Notice: Subject to any disclaimer, the term of this patent is extended or adjusted under 35 U.S.C. 154(b) by 935 days.

This patent is subject to a terminal disclaimer.

(21) Appl. No.: 17/413,991

(22) PCT Filed: Dec. 16, 2019

(86) PCT No.: PCT/EP2019/085250

§ 371 (c)(1),
(2) Date: Jun. 15, 2021

(87) PCT Pub. No.: WO2020/126979

PCT Pub. Date: Jun. 25, 2020

(65) Prior Publication Data

US 2022/0023248 A1 Jan. 27, 2022

(30) Foreign Application Priority Data

Dec. 17, 2018 (EP) .................................... 18213140

(51) Int. Cl.
*A61K 31/23* (2006.01)
*A23L 33/00* (2016.01)
(Continued)

(52) U.S. Cl.
CPC .............. *A61K 31/23* (2013.01); *A23L 33/12* (2016.08); *A23L 33/21* (2016.08); *A23L 33/40* (2016.08);
(Continued)

(58) Field of Classification Search
CPC ...... A61K 31/23; A61K 31/231; A61K 45/06; A23L 33/12; A23L 33/21; A23L 33/40; A23P 10/40; A23V 2002/00; A61P 1/12
See application file for complete search history.

(56) References Cited

U.S. PATENT DOCUMENTS 5,312,836 A 5/1994 Bistrian
5,662,953 A 9/1997 Wheeler et al.
(Continued)

FOREIGN PATENT DOCUMENTS

CN 107673970 2/2018
EP 2057902 5/2009
(Continued)

OTHER PUBLICATIONS

Shaw D, Gohil K, Basson MD. Intestinal mucosal atrophy and adaptation. World J Gastroenterol. Nov. 28, 2012;18(44):6357-75. doi: 10.3748/wjg.v18.i44.6357. PMID: 23197881; PMCID: PMC3508630. (Year: 2012).*
(Continued)

*Primary Examiner* — Bruck Kifle
*Assistant Examiner* — Kevin S Martin
(74) *Attorney, Agent, or Firm* — K&L Gates LLP

(57) ABSTRACT

A compound having the formula (1), (2), (3) or (4), or combinations thereof, for use in the prevention or treatment of dehydration, and/or in the treatment of diarrhea, wherein R1, R2, R3, R4, R5 and R6 are independently, a long chain fatty acid having between 16 and 20 carbons.

(1)

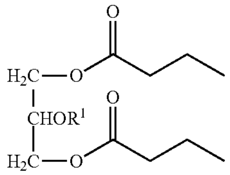

(2)

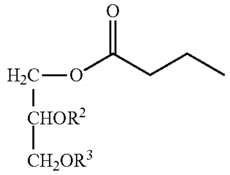

(3)

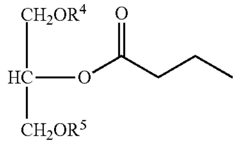

(4)

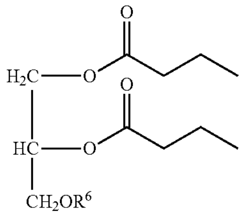

9 Claims, No Drawings

(51) Int. Cl.

| | |
|---|---|
| ***A23L 33/12*** | (2016.01) |
| ***A23L 33/21*** | (2016.01) |
| ***A23P 10/40*** | (2016.01) |
| ***A61K 31/231*** | (2006.01) |
| ***A61K 45/06*** | (2006.01) |
| ***A61P 1/12*** | (2006.01) |

(52) U.S. Cl.

CPC ............ *A23P 10/40* (2016.08); *A61K 31/231* (2013.01); *A61K 45/06* (2013.01); *A23V 2002/00* (2013.01)

(56) References Cited

U.S. PATENT DOCUMENTS

| | | | |
|---|---|---|---|
| 2016/0037818 | A1 | 2/2016 | Destaillats et al. |
| 2018/0161292 | A1 | 6/2018 | Kuang et al. |
| 2018/0332881 | A1 | 11/2018 | Lambers et al. |

FOREIGN PATENT DOCUMENTS

| | | | | |
|---|---|---|---|---|
| EP | 2057902 | A1 | 5/2009 | |
| GB | 1495493 | | 12/1977 | |
| GB | 1495493 | A | 12/1977 | |
| WO | 9109597 | | 7/1991 | |
| WO | 9109597 | A1 | 7/1991 | |
| WO | WO-9210105 | A1 * | 6/1992 | ............. A21D 2/165 |
| WO | 9412051 | | 6/1994 | |
| WO | 9412051 | A1 | 6/1994 | |
| WO | 2019228851 | A1 | 12/2019 | |

OTHER PUBLICATIONS

Medical News Today, What you should know about dehydration, 2017, https://www.medicalnewstoday.com/articles/153363. See also attached PDF. (Year: 2017).*
PubChem, Ethyl Butyrate, created 2005, https://pubchem.ncbi.nlm.nih.gov/compound/Ethyl-butyrate (Year: 2005).*
PubChem, Glyceryl Trioleate, created 2005, https://pubchem.ncbi.nlm.nih.gov/compound/TRIOLEIN (Year: 2005).*
CH 10 Fundamental in Biochemistry, Lipid Metabolism, 2008, Ed 1, pp. 343-345 (Year: 2008).*
Martin et al. "In Vitro Intestinal Bioaccessibility of Alkylglycerols Versus Triacylglycerols as Vehicles of Butyric Acid" Lipids, 2011, vol. 46, pp. 277-285.
Canani et al. "Butyrate as an Effective Treatment of Congenital Chloride Diarrhea" Gastroenterology, 2004, vol. 127, pp. 630-634.
Sen et al., "Fruit Waste Pectin in Enhancing the Establishment of Probiotic Bacteria", Journal of Nutritional Health & Food Engineering, vol. 1, Issue No. 3, 2014, pp. 124-126.
Patel et al., "The Current Trends and Future Perspectives of Prebiotics Research: A Review", 3 Biotech, vol. 2, 2012, pp. 115-125.
Garthwaite et al., "Whole Milk and Oral Rehydration Solution for Calves with Diarrhea of Spontaneous Origin", Journal of Dairy Science, vol. 77, Issue No. 3, 1994, pp. 835-843.
Kalo et al., "Determination of Triacylglycerols in Butterfat by Normal-Phase HPLC and Electrospray-Tandem Mass Spectrometry", Lipids, vol. 44, 2009, pp. 169-195.
Kemppinen et al., "Analysis of sn-1 (3)- and sn-2-Short-Chain Acyl Isomers of Triacylglycerols in Butteroil by Gas-liquid Chromatography", Journal of the American Oil Chemists' Society, vol. 75, Issue No. 2, 1998, pp. 91-100.
Shirreffs et al., "Milk as an Effective Post-Exercise Rehydration Drink", British Journal of Nutrition, vol. 98, 2007, pp. 173-180.
"Nutrient Supplement with Electrolytes for Scouring Animals", Advance Arrest, 6 Pages.
Cathers, "Final Report on the Safety Assessment of Safflower Oil", Journal of the American College of Toxicology, vol. 4, Issue No. 5, 1985, pp. 171-197.
Bockisch, Fats and Oil Handbook, 1993, p. 180.
Kotunia et al., "Effect of Sodium Butyrate on the Small Intestine Development in Neonatal Piglets Feed by Artificial Sow", Journal of Physiology and Pharmacology, vol. 55, 2004, pp. 59-68.
Scarpellini et al., "Efficacy of Butyrate in the Treatment of Diarrhoea-Predominant Irritable Bowel Syndrome", Digestive and Liver Disease, Supplements 1 (translation), 2007, pp. 19-22.
Notice of Opposition for Appl No. 19817738.8-1112 dated Oct. 12, 2023.
Guillon et al., "First Total Synthesis of 1,3-Diacetyl- and -Dibutyroyl-2-oleoylglycerol, Previously Isolated from Natural Products", Pharmacy and Pharmacology Communications, vol. 5, Issue Numbe 5, 1999, pp. 311-313.
Zhou et al., "Chemical Profiling of Triacylglycerols and Diacylglycerols in Cow Milk Fat by Ultra-performance Convergence Chromatography Combined With a Quadrupole Time-of-flight Mass Spectrometry", Food Chemistry, vol. 143, Jan. 15, 2014, pp. 199-204.
Ward et al., "Solubility of Tristearin and Hydrogenated Cottonseed Oil in Certain Aceto- and Butyroglycerides", The Journal of the American Oil Chemists' Society, vol. 32, 1954, pp. 316-318.
Japanese Office Action for Appl No. 2021-531056 dated Dec. 5, 2023.
Jensen et al., "Symposium: Milk Fat-Composition, Function, and Potential for Change", Journal of Dairy Science, vol. 74, Issue No. 9, Dec. 31, 1991, pp. 3228-3243.
Roberto Bernie Canani et al., 'Butyrate as an Effective Treatment of Congenital Chloride Diarrhea', Gastroenterology 2004; 127:630-634.
E. Scarpellini et al., 'Efficacy of butyrate in the treatment of diarrhoea-predominant irritable bowel syndrome', Digestive and Liver Disease Supplements 1 (translation) (2007) 19-22.
A. Kotunial et al., 'Effect of Sodium Butyrate on the Small Intestine Development in Neonatal Piglets Feed by Artificial Sow', Journal of Physiology and Pharmacology 2004, 55, Suppl 2, 59-68.
Ananya Sen et al., 'Fruit waste pectin in enhancing the establishment of probiotic bacteria', J Nutr Health Food Eng. 2014;1(3):124-126.
Seema Patel et al., 'The current trends and future perspectives of prebiotics research: a review', 3 Biotech (2012) 2:115-125.
B. D. Garthwaite et al., 'Whole Milk and Oral Rehydration Solution for Calves with Diarrhea of Spontaneous Origin1', Journal of Dairy Science, vol. 77, No. 3, 835-843 (1994).
P. Kala et al., 'Determination of Triacylglycerols in Butterfat by Normal-Phase HPLC and Electrospray-Tandem Mass Spectrometry', Lipids (2009) 44:169-195.
Asma Kemppinen et al., 'Analysis of sn-1(3)- and sn-2-Short-Chain Acyl Isomers of Triacylglycerols in Butteroil by Gas-Liquid Chromatography', JAOCS, vol. 75, No. 2 (1998).
Susan M. Shirreffs et al., 'Milk as an effective post-exercise rehydration drink', British Journal of Nutrition (2007), 98, 173-180.
Product label for Advance Arrest as referenced in D8.
'Final Report on the Safety Assessment of Safflower Oil', Journal of the American College of Toxicology, vol. 4, No. 5, 1985.
Extract from Fats and Oils Handbook, p. 180, (Michael Bockisch, 1993).
European Opposition for EP3897726 dated Oct. 4, 2023.
Alam et al., "Partially Hydrolyzed Guar Gum-Supplemented Oral Rehydration Solution in the Treatment of Acute Diarrhea in Children", Journal of Pediatric Gastroenterology and Nutrition, vol. 31, Issue No. 5, Nov. 2000, pp. 503-507.
Binder et al., "Role of Colonic Short-Chain Fatty Acid Transport in Diarrhea", Annual Review of Physiology, vol. 72, Mar. 2010, pp. 297-313.
Ramakrishna et al., "Amylase-Resistant Starch Plus Oral Rehydration Solution for Cholera", New England Journal of Medicine, vol. 342, Issue No. 5, Feb. 3, 2000, pp. 308-313.
Acquistapace et al., "Effects of Interesterified Lipid Design on the Short/Medium Chain Fatty Acid Hydrolysis Rate and Extent (in Vitro)", Food & Function, vol. 10, Issue No. 7, 2019, pp. 4166-4176.
European Office Action for Appl No. 19817738.8-1109 dated Jun. 10, 2024, 21 pages.
Australian Office Action for Appl No. 2019407473 dated Aug. 19, 2024, 3 pages.

(56) References Cited

OTHER PUBLICATIONS

Anbazhagan et al., “Pathophysiology of IBD Associated Diarrhea”, Tissue Barriers, vol. 06, Issue No. 02, 2018, pp. 1-21.
Ormarsson et al., “Clinical Trial: Marine Lipid Suppositories as Laxatives”, Marine Drugs, vol. 10, 2012, pp. 2047-2054.
European Office Action for Appl No. 19817738.8-1109 dated Nov. 28, 2024, 9 pages.

* cited by examiner

DIETARY BUTYRATE

CROSS REFERENCE TO RELATED APPLICATIONS

The present application is a National Stage of International Application No. PCT/EP2019/085250, filed on Dec. 16, 2019, which claims priority to European Patent Application No. 18213140.9, filed on Dec. 17, 2018, the entire contents of which are being incorporated herein by reference.

FIELD OF THE INVENTION

The present invention relates to a dietary source of butyrate having improved organoleptic properties. More particularly to the use thereof in oral rehydration solutions and in the treatment of diarrhea and/or preventing or treating dehydration.

BACKGROUND TO THE INVENTION

Salts and esters of butyric acid are known as butyrates or butanoates. Butyric acid in ester form is found in many foods such as milk, especially goat, sheep, cow, camel and buffalo milk, and milk-derived products such as butter as well as cheeses such as parmesan cheese. Butyric acid is also a product of anaerobic fermentation, for example, as a product of fermentation produced by gut microbiota.

Multiple beneficial effects of butyrate are well documented in mammals and livestock. At the intestinal level, butyrate plays a regulatory role on the transepithelial fluid transport, ameliorates mucosal inflammation and oxidative status, reinforces intestinal barrier function, and influences visceral sensitivity and intestinal motility.

Butyrate has been shown to decrease the incidence of diarrhea (Berni Canani et al., Gastroenterol., 2004; 127(2): 630-634). Butyrate has also been reported to improve inflammatory bowel disease (Scarpellini et al., Dig Liver Dis., 2007; 1(1):19-22) and small intestine health (Kotunia et al., J Physiol Pharmacol. 1994; 55(2):59-68).

Tributyrin is a triglyceride made of three ester functional groups with three butyrate moieties and the glycerol backbone. Under hydrolysis conditions such as those occurring during digestion, tributyrin is potentially a source of three moles of butyric acid per mole of tributyrin.

Butyric acid and tributyrin are both food additives that are generally regarded as safe (GRAS) (21CFR582.60 and 21CFR184.1903 respectively), and are natural components of many dairy items. However, butyric acid is associated with negative sensory qualities such as vomit-like, fecal, and cheesy aroma attributes. Tributyrin also has negative sensory qualities, in particular high bitterness. These unpleasant taste and odor attributes can make the oral administration of compositions including these compounds particularly difficult, especially in the pediatric population.

Oral rehydration solutions are widely used for prevention and treatment of dehydration due to diarrhea and other causes, such as fever, produced by illness, increase in perspiration, high exposure to sun or hot environment, intense movement (of babies), increase in saliva due to teething, work which involves a high loss of liquids (in adults).

Oral rehydration solutions are balanced electrolyte solutions designed to replace fluids and minerals (e.g., sodium, potassium), e.g. lost due to diarrhea and/or vomiting. Some existing oral rehydration solutions also include prebiotics such as partially hydrolyzed guar gum for the generation of short chain fatty acids that potentiate the effect of ORS, reducing the severity of diarrhea (Alam N H et al., J Pediatr Gastroenterol Nutr. 2000 November; 31(5):503-7). The addition of prebiotics relies on the activity of the microbiota in the colon to metabolise the prebiotics for the production of short-chain fatty acids (SOFA), which include but are not restricted to acetic, propionic and butyric acid, in the colon. However, the activity of the microbiota in the colon may be impeded due to diarrhea.

As such, there remains a need for compositions and methods for treating diarrhea and/or preventing or treating dehydration.

SUMMARY OF THE INVENTION

The present invention provides compounds that are a source of butyrate having improved organoleptic properties, which may be used in treating diarrhea and/or preventing or treating dehydration. In particular, the compounds have improved odor and/or taste relative to butyric acid, butyrate salts and tributyrin. The compounds may be used in combination with an oral rehydration formulation or as part of an oral rehydration formulation. The compounds may be used in, for example, nutritional compositions, dietary supplements, infant formulas and follow-on formulas.

According to a first aspect of the present invention there is provided a compound having the formula (1)

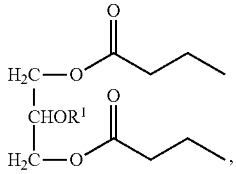

, (2)

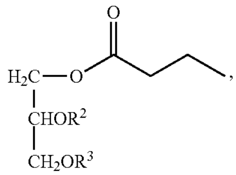

, (3)

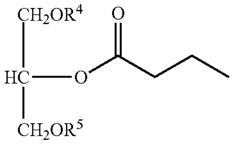

or (4)

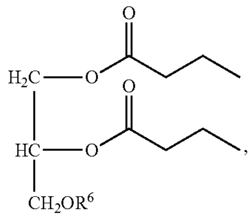

, or combinations thereof, for use in preventing or treating dehydration, wherein $R^1$, $R^2$, $R^3$, $R^4$, $R^5$ and $R^6$ are independently, a long chain fatty acid having between 16 and 20 carbons.

In an embodiment the dehydration is dehydration due to diarrhea.

According another aspect of the present invention there is provided a compound having the formula (1)

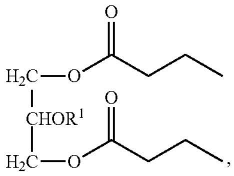

(2)

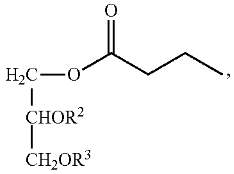

(3)

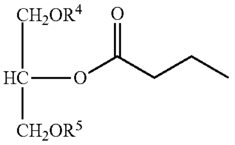

or (4)

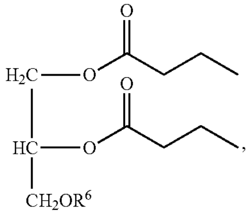

or combinations thereof, for use in treating diarrhea, wherein $R^1$, $R^2$, $R^3$, $R^4$, $R^5$ and $R^6$ are independently, a long chain fatty acid having between 16 and 20 carbons.

The compounds of formulas (1), (2), (3) and/or (4) may be used, for example, as part of an oral hydration solution or in combination with an oral hydration solution.

The compounds of formulas (1), (2), (3) and/or (4) may be present in, for example, a composition such as a nutritional formulation, a dietary supplement, an infant formula, follow on formula.

In an embodiment the compounds of formulas (1), (2), (3) and/or (4) may be used in combination with a prebiotic, for example oligosaccharides, such as fructooligosaccharides (FOS), inulin, xylooligosaccharides (XOS), polydextrose or any mixture thereof. In a particular embodiment, the prebiotics may be fructooligosaccharides and/or inulin. In a specific embodiment, the prebiotics is a combination of FOS with inulin such as in the product sold by BENEO-Orafti under the trademark Orafti® oligofructose (previously Raftilose®) or in the product sold by BENEO-Orafti under the trademark Orafti® inulin (previously Raftiline®). Another example is a combination of 70% short chain fructooligosaccharides and 30% inulin, which is registered by Nestle under the trademark "Prebio 1". In a particular embodiment the prebiotic is partially hydrolyzed guar gum (PHGG).

The compounds of the invention advantageously provide a food-grade source of butyrate having improved organoleptic properties as compared to available solutions. In one embodiment, the improved organoleptic properties are improved odour. In one embodiment, the improved organoleptic properties are improved taste. In one embodiment, the improved organoleptic properties are improved odour and improved taste. In one embodiment, the improved taste is reduced bitterness.

According to another aspect of the present invention there is provided an oral rehydration solution comprising a compound having the formula (1)

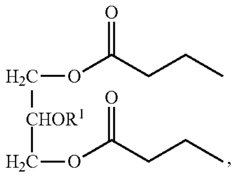

(2)

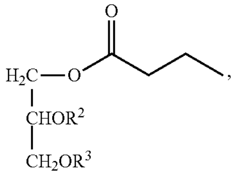

(3)

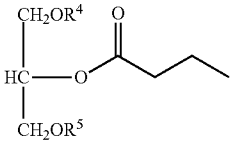

or (4)

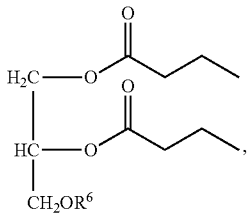

or combinations thereof, wherein $R^1$, $R^2$, $R^3$, $R^4$, $R^5$ and $R^6$ are independently, a long chain fatty acid having between 16 and 20 carbons.

The oral hydration formulation may be in the form of, for example, a powder for reconstitution or a liquid.

According to another aspect of the present invention there is provided a method of treating diarrhea and/or preventing or treating dehydration in an individual in need thereof comprising administering an effective amount of a compound having the formula (1)

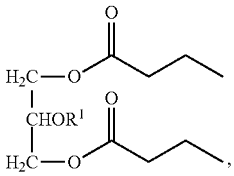

-continued (2)

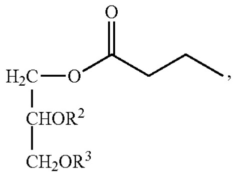

(3)

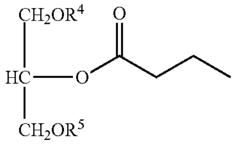

or (4)

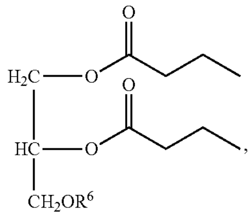

or combinations thereof to said individual, wherein $R^1$, $R^2$, $R^3$, $R^4$, $R^5$ and $R^6$ are independently, a long chain fatty acid having between 16 and 20 carbons.

In one embodiment, a combination of a compound having formula (1) and a compound having formula (2) is used as defined herein, or is present in the composition (e.g., nutritional composition, dietary supplement, infant formula or follow on formula) as defined herein. Preferably the compound having formula (1) is present in an amount of at least 10% by weight of the total triglycerides in the composition, and the compound having formula (2) is present in an amount of at least 10% by weight of the total triglycerides in the composition.

In one embodiment a combination of a compound having formula (1) and a compound having formula (2) is used as defined herein, or is present in the composition (e.g. nutritional composition, dietary supplement, infant formula or follow-on formula) as defined herein, wherein the compound having formula (1) is present in an amount of at least 10% by weight of the total butyric acid containing triglycerides in the composition, and the compound having formula (2) is present in an amount of at least 10% by weight of the total butyric acid containing triglycerides in the composition.

In another embodiment a combination of a compound having formula (1) and a compound having formula (2) is used as defined herein, or is present in the composition (e.g., nutritional composition, dietary supplement, infant formula or follow on formula) as defined herein wherein the compound having formula (1) is present in an amount of at least 15% by weight of the total butyric acid containing triglycerides in the composition, and the compound having formula (2) is present in an amount of at least 15% by weight of the total butyric acid containing triglycerides in the composition.

In one embodiment a combination of a compound having formula (1), a compound having formula (2), a compound having formula (3) and a compound having formula (4) is used as defined herein, or is present in the oral rehydration solution, nutritional composition, dietary supplement, infant formula or follow on formula as defined herein.

In one embodiment, the compound having the formula (4) is the main butyrate moiety containing triglyceride in the composition (e.g., oral rehydration solution, nutritional composition, dietary supplement, infant formula or follow on formula) as defined herein.

In one embodiment, the compound of formula (4) comprises at least 20%, at least 30%, at least 40%, at least 50%, or at least 60%, at least 70%, at least 80% or at least 90%, by weight of the total butyrate moiety containing triglycerides in the composition.

In one embodiment, the composition comprises the compound of formula (1) and the compound of formula (4), and the combination of the compound having formula (1) and the compound having the formula (4) is present in an amount of at least 30%, 40%, 50%, 60%, 70%, 80%, or 90% by weight of the total butyrate moiety containing triglycerides in the composition.

In one embodiment, $R^1$, $R^2$, $R^3$, $R^4$, $R^5$ and/or $R^6$ as defined herein is an unsaturated fatty acid, preferably monounsaturated.

In one embodiment, $R^1$, $R^2$, $R^3$, $R^4$, $R^5$ and/or $R^6$ as defined herein is selected from the group consisting of oleic acid, palmitic acid, stearic acid or linoleic acid.

In one embodiment, $R^1$, $R^2$, $R^3$, $R^4$, $R^5$ and/or $R^6$ as defined herein is oleic acid.

In one embodiment, $R^1$, $R^2$, $R^3$, $R^4$, $R^5$ and/or $R^6$ as defined herein is palmitic acid.

In one embodiment the compound (1) is 1,3-dibutyryl-2-palmitoylglycerol.

In one embodiment, each of $R^1$, $R^2$, $R^3$, $R^4$, $R^5$ and $R^6$ is oleic acid.

In one embodiment, the compound having the formula (1) is:

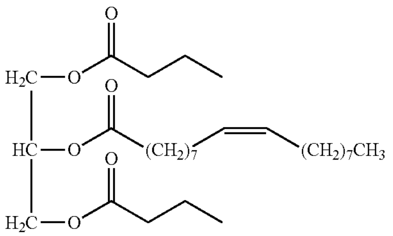

In one embodiment, the compound having the formula (2) is:

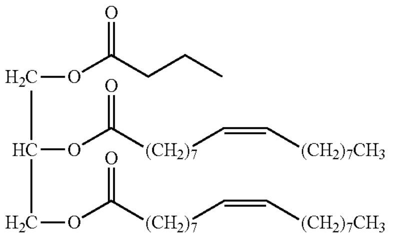

In one embodiment, the compound having the formula (3) is:

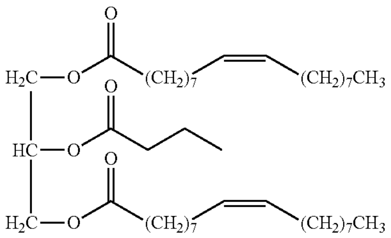

In one embodiment, the compound having the formula (4) is:

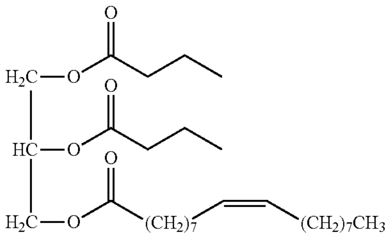

According to another aspect of the present invention there is provided a composition comprising compounds having the formulas (5)

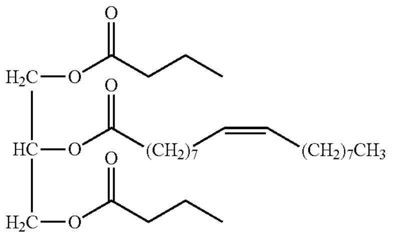

and (6)

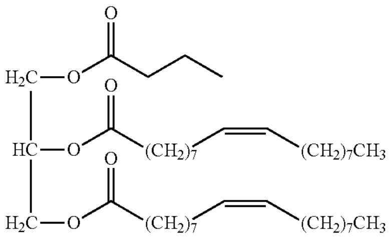

for use in treating diarrhea and/or preventing or treating dehydration, wherein the compound having formula (5) comprises at least 10% by weight of the total triglycerides in the composition, and the compound having formula (6) comprises at least 10% by weight of the total triglycerides in the composition.

In one embodiment the compound having formula (5) comprises at least 15% by weight of the total triglycerides in the composition, and the compound having formula (6) comprises at least 15% by weight of the total triglycerides in the composition.

In one embodiment the compound having formula (5) comprises at least 15% by weight of the total triglycerides in the composition, and the compound having formula (6) comprises at least 20% by weight of the total triglycerides in the composition.

In one embodiment the compound having formula (5) comprises at least 20% by weight of the total triglycerides in the composition, and the compound having formula (6) comprises at least 20% by weight of the total triglycerides in the composition.

In one embodiment the compound having formula (5) comprises about 15% to about 30% by weight of the total triglycerides in the composition, and the compound having formula (6) comprises about 20% to about 30% by weight of the total triglycerides in the composition.

In one embodiment the composition further comprises a compound having the formula (7)

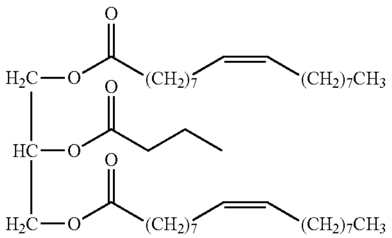

preferably wherein the compound having formula (7) comprises at least 2% or 3% by weight of the total triglycerides in the composition, and/or further comprises a compound having the formula (8)

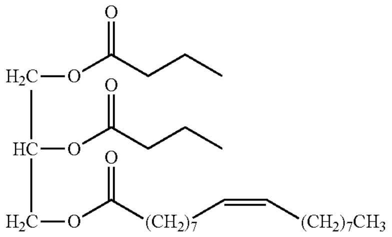

preferably wherein the compound having formula (8) comprises at least 2% or 3% by weight of the total triglycerides in the composition.

According to another embodiment of the present invention there is provided a composition comprising compounds having the formulas (5)

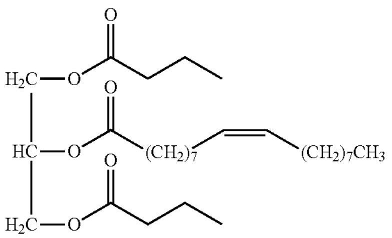

and

-continued (6)

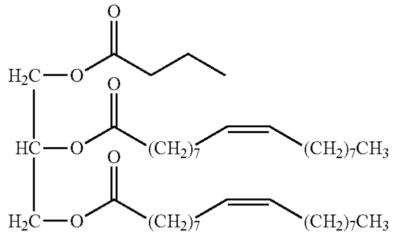

for use in treating diarrhea and/or preventing or treating dehydration, wherein the compound having formula (5) comprises at least 10% by weight of the total butyrate moiety containing triglycerides in the composition, and the compound having formula (6) comprises at least 10% by weight of the total butyrate moiety containing triglycerides in the composition.

In one embodiment, the compound having formula (5) comprises at least 15% by weight of the total butyrate moiety containing triglycerides in the composition, and the compound having formula (6) comprises at least 15% by weight of the total butyrate moiety containing triglycerides in the composition.

In one embodiment, the compound having formula (5) comprises at least 15%, preferably at least 20% by weight of the total butyrate moiety containing triglycerides in the composition, and the compound having formula (6) comprises at least 20%, preferably at least 25% by weight of the total butyrate moiety containing triglycerides in the composition.

In one embodiment the composition further comprises a compound having formula (7), preferably wherein the compound having formula (7) comprises at least 2% or 3% by weight of the total butyrate moiety containing triglycerides in the composition, and/or further comprises the compound having formula (8), preferably wherein the compound having formula (8) comprises at least 2% or 3% by weight of the total butyrate moiety containing triglycerides in the composition.

In another embodiment, the compound having the formula (8) is the main butyrate moiety containing triglyceride in the composition.

In one embodiment, the compound of formula (8) comprises at least 20%, at least 30%, at least 40%, at least 50%, or at least 60%, at least 70%, at least 80% or at least 90%, by weight of the total butyrate moiety containing triglycerides in the composition.

In one embodiment the compound having formula (8) comprises about 20% to about 95% by weight of the total butyrate moiety containing triglycerides in the composition, for example about 30% to about 90%, or about 40% to about 80% by weight of the total butyrate moiety containing triglycerides in the composition, for example about 50% to about 70% by weight of the total butyrate moiety containing triglycerides in the composition.

In one embodiment the compound having formula (8) comprises about 50% to about 90% by weight of the total butyrate moiety containing triglycerides in the composition, for example about 60% to about 80% by weight of the total butyrate moiety containing triglycerides in the composition.

In one embodiment, the composition comprises the compound of formula (8) and the compound of formula (5), and the combination of the compound having formula (8) and the compound having the formula (5) is present in an amount of at least 30%, 40%, 50%, 60%, 70%, 80%, or 90% by weight of the total butyrate moiety containing triglycerides in the composition.

The composition of the present invention may further comprise 1,3-dibutyryl-2-linoleoylglycerol, 1,3-dibutyryl-2-stearoylglycerol, 1-butyryl-2-oleoyl-3-palmitoylglycerol, 1-palmitoyl-2-oleoyl-3-butyrylglycerol, 1-butyryl-2-oleoyl-3-linoleoylglycerol, 1-linoleoyl-2-oleoyl-3-butyrylglycerol, 1-oleoyl-2-butyryl-3-linoleoylglycerol, 1-linoleoyl-2-butyryl-3-oleoylglycerol, 1-butyryl-2-linoleoyl-3-oleoylglycerol, 1-oleoyl-2-linoleoyl-3-butyrylglycerol, 1-butyryl-2-stearoyl-3-oleoylglycerol, 1-oleoyl-2-stearoyl-3-butyrylglycerol, 1-butyryl-2-oleoyl-3-stearoylglycerol, 1-stearoyl-2-oleoyl-3-butyrylglycerol, 1,2-dioleoyl-3-palmitoylglycerol, 1-palmitoyl-2,3-dioleoylglycerol, 1,2-dioleoyl-3-linoleoylglycerol and/or 1-linoleoyl-2,3-dioleoylglycerol.

The composition of the present invention may be in the form of an oral rehydration formulation.

The composition of the present invention may be in the form of a nutritional composition, a dietary supplement an infant formula or follow on formula.

The composition of the present invention may further comprise a prebiotic. In a preferred embodiment the prebiotic is partially hydrolysed guar gum (PHGG).

According to another aspect of the present invention there is provided a method of treating diarrhea in a subject in need thereof, comprising administering an effective amount of a composition defined herein to the subject.

According to another aspect of the present invention there is provided a method of preventing or treating dehydration in a subject in need thereof, comprising administering an effective amount of a composition defined herein to the subject.

According to one embodiment of the present invention there is provided a method of preventing or treating dehydration due to diarrhea in a subject in need thereof, comprising administering an effective amount of a composition defined herein to a the subject.

DETAILED DESCRIPTION OF THE INVENTION

Triglycerides

A triglyceride (also known as a triacylglycerol) is a triester that is derived from glycerol and three fatty acids.

Fatty acids are carboxylic acids with a long tail (chain). Fatty acids may be either unsaturated or saturated. Fatty acids which are not attached to other molecules are referred to as free fatty acids (FFA).

The term "fatty acid moiety" refers to the part of the triglyceride that originates from a fatty acid in an esterification reaction with glycerol The triglycerides used in the present invention comprise at least one butyric acid moiety and at least one long chain fatty acid moiety.

Preferred long chain fatty acids for use in the present invention are fatty acids that have 16 to 20 carbon atoms.

Examples of long chain fatty acid include oleic acid, palmitic acid, stearic acid and linoleic acid.

The triglycerides of the present invention may be synthesised by, for example, esterification of long chain fatty acid(s) and butyric acid with glycerol.

The triglycerides of the present invention may be synthesised by, for example, interesterification between tributyrin and another triglyceride containing long chain fatty acids. In one embodiment, high oleic sunflower oil is the source of the long chain fatty acids. This generates triglycerides containing predominantly butyrate and oleate moieties. Oleic acid is the predominant fatty acid present in breast milk. The compounds are dairy-free, cholesterol-free and vegan. Fatty acids are liberated from triglycerides due to lipases, naturally present in the gastrointestinal tract. Relative to butyrate salts, the compounds do not add additional mineral salts to the final formulation.

Alternative methods of triglyceride synthesis can be routinely determined by a person skilled in the art. By way of example, a method of obtaining 1,3-dibutyryl-2-palmitoylglycerol (BPB) is shown below:

≥2; i.e. in a molar excess of butyric acid. Removal of water can be carried by conventional methods, routinely used in the art.

A single butyrate moiety containing triglyceride may be used herein. Alternatively, a mixture of different butyrate moiety containing triglycerides may be used.

The triglycerides may be further subjected to decolouration and/or deodorization steps conventional in the art and well known to the person skilled in the art. For example, as conventionally used in the manufacture of vegetable oils.

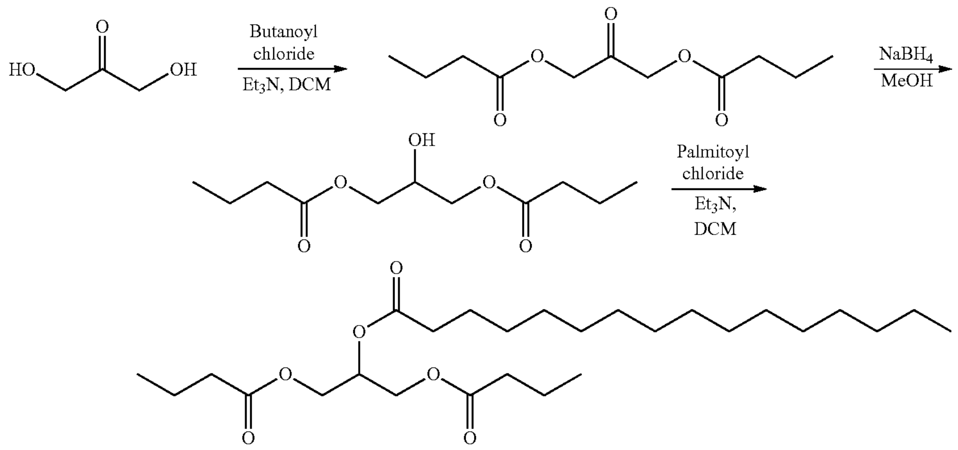

As another example, the triglycerides may be synthesized by esterification of a long chain fatty acid monoacylglycerol (MAG) with butyric acid (BA).

For example, by esterification of long chain fatty acid monoacylglycerol (MAG) with butyric acid (BA) with the removal of water. By way of example a method of obtaining 1,2-dibutyryl-3-oleoylglycerol is shown below:

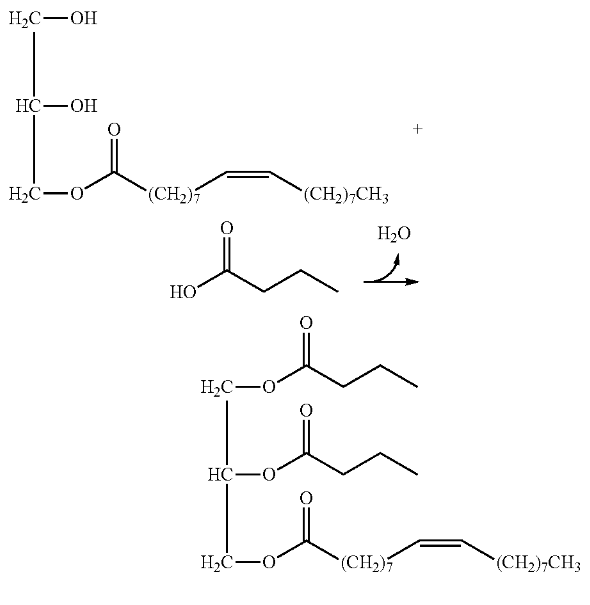

The esterification reaction is preferably carried out with butyric acid (BA): monoacylglycerol (MAG) molar ratio of Compositions The present invention provides compositions comprising butyrate moiety containing triglycerides referred to herein. The composition may be, for example, an oral rehydration solution, a nutritional composition, a dietary supplement, an infant formula or a follow-on formula.

As used herein, an "oral rehydration solution" refers to a composition for use in oral rehydration therapy to replace fluids and electrolytes (e.g., sodium, potassium) lost by an individual, for example due to diarrhea and/or vomiting.

The expression "nutritional composition" means a composition that nourishes a subject. This nutritional composition is preferably taken orally, and it may include a lipid or fat source and a protein source. It may also contain a carbohydrate source. In one embodiment, the nutritional composition contains only a lipid or fat source. In other specific embodiments, the nutritional composition contains a lipid (or fat) source with a protein source, a carbohydrate source or both.

In some specific embodiments, the nutritional composition according to the invention is an "enteral nutritional composition" that is to say a foodstuff that involves the gastrointestinal tract for its administration. The gastric introduction may involve the use of a tube through the oro/nasal passage or a tube in the belly leading directly to the stomach. This may be used especially in hospitals or clinics.

The composition according to the invention can be an infant formula (e.g. a starter infant formula), a follow-up or follow-on formula, a growing-up milk, a baby food, an infant cereal composition, a fortifier such as a human milk fortifier, or a supplement.

The expression "infant formula" as used herein refers to a foodstuff intended for particular nutritional use by infants during the first months of life and satisfying by itself the nutritional requirements of this category of person (e.g., Article 2(c) of the European Commission Directive 91/321/EEC 2006/141/EC of 22 Dec. 2006 on infant formulae and follow-on formulae).

Generally a starter formula is for infants from birth as breast-milk substitute. A follow-up or follow-on formula is given from the sixth month onwards. It constitutes the principal liquid element in the progressively diversified diet of this category of person. The "growing-up milks" (or GUMs) are given from one year onwards. It is generally a milk-based beverage adapted for the specific nutritional needs of young children.

The term "dietary supplement" may be used to complement the nutrition of an individual (it is typically used as such but it might also be added to any kind of compositions intended to be ingested). It may be in the form of tablets, capsules, pastilles or a liquid for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The dietary supplement may also contain conventional pharmaceutical additives and adjuvants, excipients and diluents, including, but not limited to, water, gelatine of any origin, vegetable gums, lignin-sulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

When the composition is a supplement, it can be provided in the form of unit doses.

The composition of the invention can further comprise at least one non-digestible oligosaccharide (e.g. prebiotics). They are usually in an amount between 0.3 and 10% by weight of composition.

Prebiotics are usually non-digestible in the sense that they are not broken down and absorbed in the stomach or small intestine and thus remain intact when they pass into the colon where they are selectively fermented by the beneficial bacteria. Examples of prebiotics include certain oligosaccharides, such as fructooligosaccharides (FOS), inulin, xylooligosaccharides (XOS), polydextrose or any mixture thereof. In a particular embodiment, the prebiotics may be fructooligosaccharides and/or inulin. In a specific embodiment, the prebiotics is a combination of FOS with inulin such as in the product sold by BENEO-Orafti under the trademark Orafti® oligofructose (previously Raftilose®) or in the product sold by BENEO-Orafti under the trademark Orafti® inulin (previously Raftiline®). Another example is a combination of 70% short chain fructooligosaccharides and 30% inulin, which is registered by Nestle under the trademark "Prebio 1". In a particular embodiment the prebiotic is partially hydrolyzed guar gum (PHGG)

The composition of the present invention can be in, for example, a solid (e.g. powder) for rehydration or liquid form.

The composition may in the form of a pharmaceutical composition and may comprise one or more suitable pharmaceutically acceptable carriers, diluents and/or excipients.

Examples of such suitable excipients for compositions described herein may be found in the "Handbook of Pharmaceutical Excipients", 2nd Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

The pharmaceutical compositions may comprise as, or in addition to, the carrier, excipient or diluent any suitable binder(s), lubricant(s), suspending agent(s), coating agent(s) and/or solubilising agent(s). Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilisers, dyes and even flavouring agents may be provided in the composition. Examples of preservatives include sodium benzoate, sorbic acid and esters of p-hydroxybenzoic acid. Antioxidants and suspending agents may be also used.

Uses

The multiple beneficial effects on gastrointestinal (GI) health of butyrate are well documented. At the intestinal level, butyrate plays a regulatory role on the transepithelial fluid transport, ameliorates mucosal inflammation and oxidative status, reinforces the epithelial defense barrier, and modulates visceral sensitivity and intestinal motility. Delivery of butyrate in salt form has been shown to reduce the severity of diarrhea (Berni Canani et al., Gastroenterol., 2004; 127(2):630-634).

The compounds defined herein are a source of butyrate and may therefore be used for treating diarrhea and/or for preventing or treating dehydration associated with diarrhea.

In one embodiment, the compounds and compositions defined herein may be used in the treatment of diarrhea.

In one embodiment, the compounds and compositions defined herein may be used in the treatment or prevention of dehydration.

Administration of the compounds of the invention will provide delivery of butyrate to the small intestine as these triglyceride compounds will be digested by gastric and pancreatic enzymes releasing the free fatty acids. Administration of the compounds defined herein as part of an ORS or in combination with ORS advantageously provides delivery of butyrate to the small intestine, By delivering butyrate directly to the small intestine, which is where the majority of fluid absorption occurs and is also the site of action of ORS, the compounds of the invention may provide an even better effect for reducing diarrhea and potentiating the effects of the ORS for treating or preventing dehydration as compared to ORS with prebiotics which require activity of the colon microbiota for producing of SOFA.

In one embodiment, the compounds and compositions defined herein may be used for preventing or treating dehydration due to diarrhea.

In a preferred embodiment, the compounds defined herein are used in combination with an oral rehydration solution (ORS). The compounds defined herein may be administered as part of an ORS or may administered separately to the ORS. The ORS and the compounds defined herein may be administered together or sequentially.

Administration

Preferably, the compounds and compositions described herein are administered enterally.

Enteral administration may be oral, gastric, and/or rectal.

In general terms, administration of the combination or composition described herein may, for example, be by an oral route or another route into the gastro-intestinal tract, for example the administration may be by tube feeding.

In a preferred embodiment the administration is oral.

The subject may be a mammal such as a human, canine, feline, equine, caprine, bovine, ovine, porcine, cervine and primates. Preferably the subject is a human.

EXAMPLES

Example 1—Preparation of Butyrated Triglycerides (TAG)

Compositions comprising butyrated TAG were generated by chemical interesterification between tributyrin and high oleic sunflower oil in the presence of catalyst such as sodium methoxyde. A molar excess of tributyrin compared to high oleic sunflower oil was be used.

The three reagents, tributyrin, high oleic sunflower oil and the catalyst were mixed together into a reactor under nitrogen atmosphere and then heat under stirring at 80° C. for 3 h. Once the reaction is completed, the product was washed with water and brine and dried under vacuum (25 mBar at 60° C. for 2 h). The resulting oil product was then subjected to a decoloration step with the action of bleaching earth and was purified either by short-path distillation (130° C., 0.001-0.003 mbar) or by deodorisation (160° C., 2 mbar, 2 h) with injection of steam water.

The constituents, mostly triglycerides, of the resulting oil compositions are shown below in Table 1. These triglycerides are represented by the three fatty acids they contain. These fatty acids are represented by their lipid number: 4:0 for butyrate, 16:0 for palmitate, 18:0 for stearate 18:1 for oleate and 18:2 for linoleate. The fatty acid in the middle is located on the position sn-2 in the triglyceride. As an example, 16:0-4:0-18:1 stands for two different triglycerides having both a butyrate in position sn-2 and either a palmitate in position sn-1 and an oleate in position sn-3 or an oleate in position sn-1 and a palmitate in position sn-3.

TAG profile and regioisomers were analyzed by liquid chromatography coupled to high resolution mass spectrometer. Lipid classes' proportion was evaluated by liquid chromatography coupled to evaporative light scattering detector (ELSD).

TABLE 1

| TAG regioisomer profile [g/100 g] | Composition |
|---|---|
| 4:0-4:0-4:0 | <0.4-4.7 |
| 4:0-16:0-4:0 | 0.8-1.0 |
| 4:0-18:2-4:0 | 4.0-6.3 |
| 4:0-4:0-18:1 | 3.0-6.1 |
| 4:0-18:1-4:0 | 16.2-27.0 |
| 4:0-18:0-4:0 | 0.8-1.3 |
| 4:0-22:0-4:0 | ≤0.4 |
| 4:0-16:0-18:1 | 1.1-1.5 |
| 16:0-4:0-18:1 | 0.5-0.7 |
| 4:0-18:1-16:0 | 1.2-1.6 |
| 4:0-18:1-18:2 | 2.6-3.1 |
| 18:1-4:0-18:2 | 1.1-1.6 |
| 4:0-18:2-18:1 | 2.9-3.6 |

TABLE 1-continued

| TAG regioisomer profile [g/100 g] | Composition |
|---|---|
| 18:1-18:1-4:0 | 23.3-25.8 |
| 18:1-4:0-18:1 | 3.3-4.8 |
| 4:0-18:0-18:1 | 0.9-1.3 |
| 4:0-18:1-18:0 | 0.8-1.1 |
| 4:0-22:0-18:1 | <0.4-0.5 |
| 18:1-18:1-16:0 | 0.6-1.4 |
| 18:1-18:1-18:2 | 1.3-1.5 |
| 18:1-18:2-18:1 | 0.5-0.7 |
| 18:1-18:1-18:1 | 6.1-10.7 |
| 18:1-18:1-18:0 | 0.5-0.8 |
| Total | 93.1-94.1 |

In the Composition samples, the two most abundant TAG are 4:0-18:1-4:0 and 18:1-18:1-4:0, they represent together approximately 40 to 50 g/100 g.

Example 2—Odor Properties of Butyrate Moiety Containing Triglycerides

An odor comparison of a solution including butyrate moiety containing TAG (composed mainly with oleic and butyric fatty acids) was compared to a solution containing sodium butyrate.

Sample Preparation

Solutions including butyrate moiety containing TAG (see Example 1) or sodium butyrate were prepared and stored at 4° C. prior to delivery to the sensory panel. Each 250 mL solution contained 600 mg of butyric acid (equivalent to one capsule of commercially available sodium butyrate as a supplement; 2.4 mg/mL concentration) and 1% w/v BEBA Optipro 1 infant formula in acidified, deionized water.

The samples were prepared the day before the test, by putting 4 mL of each solution (TAG butyrate solution; sodium butyrate solution) in Agilent vials.

Methodology

The 'two-out-of-five test' was performed. In this test, the panellist is given five samples. The panellist is instructed to identify the two samples that are different from the other three. The presentation order of the samples is randomized in order to avoid presentation order bias.

In addition to the two-out-of-five test, a comment box was presented to the panellists to allow them to comment about the nature of the difference perceived (e.g. odour intensity, odour quality).

Results

The five samples were presented simultaneously to the panellists. They were asked to uncap, smell and then cap each vial in a given order. The results are shown in Table 2.

TABLE 2

| Number of responses | Number of correct responses | Significance |
|---|---|---|
| 11 | 9 | $p < 0.0001$*** |

P-value was calculated using a binomial test performed with Fizz software (Biosystemes, France).

The panellists who found the correct responses (butyrate moiety containing TAG different from sodium butyrate) mentioned that the sodium butyrate smells "cheese" whereas for the butyrate moiety containing TAG samples this "cheese" smell was considerably decreased and the odour was quite neutral.

Example 3—Taste Properties of Butyrate Moiety Containing Triglycerides

Sensory benchmarking of a solution including butyrate moiety containing TAG (see Example 1) composed mainly with oleic and butyric fatty acids was performed versus a solution containing tributyrin.

Sample Preparation:

One scoop (4.6 g) of BEBA Optipro 1 infant formula was added to warm water (cooled, boiled tap water as per instructions) to a final volume of 150 mL (approximately 3% w/v solution).

Each TAG form of butyrate was weighed separately to deliver 600 mg of butyrate, and the addition of infant formula to a final volume of 50 mL for each solution was performed.

Solution A included butyrate moiety containing TAG (see Example 1); and solution B contained tributyrin.

Methodology

A group of panellists performed a repeated blind-coded tasting.

The samples were prepared just prior to the preliminary bitterness assessment, and each solution was vigorously shaken. Tasting cups labelled A and B were filled at the same time with a small volume of the respective solution.

The two samples were presented simultaneously to the panellists. They were asked to taste the solution in a sip and spit fashion, and rank the perceived bitterness on a scale from 0-10; where 0 is no bitterness perceived and 10 resembles the maximum imaginable bitterness.

Results

Bitterness of Solution A was ranked by panellists at 4.33±1.52, mean±SD.

Bitterness of Solution B was ranked by panellists at 8.33±1.52, mean±SD.

These data show that the butyrate moiety containing TAG composition in infant formula was notably less bitter in taste as compared to tributyrin in infant formula.

Example 4—Taste Properties 1,3-dibutyryl-2-palmitoylglycerol 1,3-dibutyryl-2-palmitoylglycerol (BPB) was synthesized as a single compound using the following synthesis:

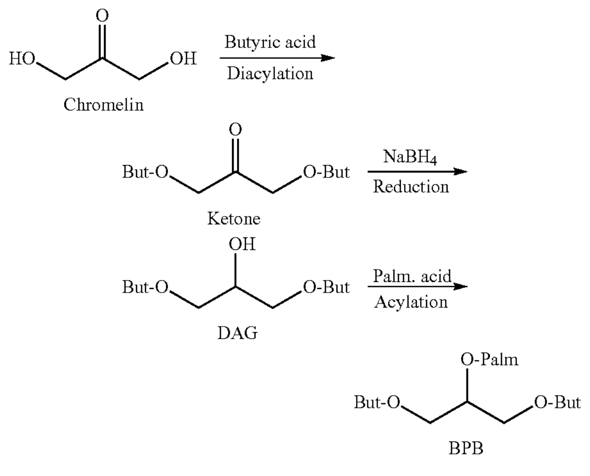

Chromelin
Ketone
DAG
BPB

BPB was evaluated in a descriptive sensory panel evaluation and found to be neutral in taste and odor.

Example 5—Preparation of Butyrated Triglycerides (TAG)

Compositions comprising butyrate moiety containing triglycerides were generated by the esterification reaction between monoolein (derived from sunflower oil) with butyric acid added in molar excess (5 equivalents in total). These two reagents were mixed together in a flask and heated to reflux (butyric acid boiling point is 163.5° C.). A condenser ("colonne de Vigreux") was used to remove the water. The reaction was monitored by TLC and stopped when all the monoacylglycerol was converted into triacylglycerol.

The constituents, mostly triglycerides, of the resulting oil compositions are shown below in Table 3. As in Example 1, the triglycerides are represented by the three fatty acids they contain. These fatty acids are represented by their lipid number: 4:0 for butyrate, 16:0 for palmitate, 18:0 for stearate 18:1 for oleate and 18:2 for linoleate. The fatty acid in the middle is located on the position sn-2 in the triglyceride.

TABLE 3

| Triglyceride profile [% by weight] | |
|---|---|
| 4:0-4:0-18:1&4:0-18:1-4:0 | 65.64 |
| 18:1-18:1-4:0&18:1-4:0-18:1 | 12.53 |
| 4:0-4:0-18:2&4:0-18:2-4:0 | 5.43 |
| 4:0-4:0-18:0&4:0-18:0-4:0 | 3.03 |
| 4:0-18:1-18:2&isomers | 2.98 |
| 4:0-16:0-18:1&isomers | 1.69 |
| 4:0-4:0-16:0&4:0-16:0-4:0 | 1.40 |
| 4:0-4:0-4:0 | 1.36 |
| 4:0-18:0-18:1&isomers | 0.99 |
| 4:0-4:0-22:0&4:0-22:0-4:0 | 0.82 |
| 18:1-18:1-18:1 | 0.63 |
| 4:0-22:0-18:1&isomers | 0.33 |
| 4:0-4:0-24:0&4:0-24:0-4:0 | 0.31 |
| 4:0-4:0-20:0&4:0-20:0-4:0 | 0.28 |
| 4:0-16:0-18:0&isomers | 0.25 |
| 18:0-18:0-16:0 | 0.22 |
| 4:0-16:0-18:2&isomers | 0.21 |
| 4:0-4:0-20:1&4:0-20:1-4:0 | 0.20 |
| 18:1-18:1-18:2 | 0.17 |
| 18:2-18:2-4:0&18:2-4:0-18:2 | 0.17 |
| 18:0-18:0-4:0&18:0-4:0-18:0 | 0.16 |
| 16:0-16:0-4:0&16:0-4:0-16:0 | 0.14 |
| 16:0-18:0-16:0 | 0.12 |
| 4:0-4:0-18:3&4:0-18:3-4:0 | 0.11 |
| 4:0-4:0-16:1&4:0-16:1-4:0 | 0.11 |

In the composition, 4:0-4:0-18:1 was identified as the most abundant triglyceride.

The resulting oil product was then subjected to a decoloration step with the action of bleaching earth and was purified either by short-path distillation (130° C., 0.001-0.003 mbar) and/or by deodorisation (160° C., 2 mbar, 2 h) with injection of steam water, to remove residual reagents and intermediates e.g. butyric acid, MAG and byproducts e.g. DAG and tributyrin.

The resulting oil product was evaluated in a descriptive sensory evaluation and found to have a better odor and taste than tributyrin and butyric acid.

The invention claimed is:

1. A method for the prevention or treatment of dehydration due to diarrhea in a subject in need thereof, the method comprising orally administering to the subject a compound having a formula selected from the group consisting of:

(1)

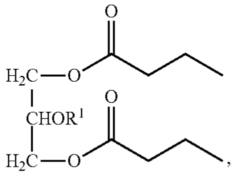

, (2)

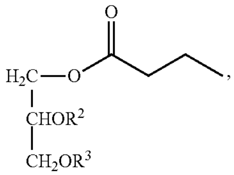

, (3)

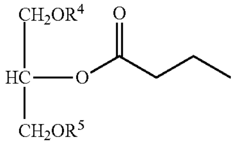

or (4)

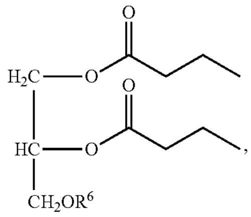

, or combinations thereof, wherein $R^1$, $R^2$, $R^3$, $R^4$, $R^5$ and $R^6$ are independently, a long chain fatty acid having from 16 to 20 carbons to the subject.

2. The method according to claim 1, wherein the method comprises administering the compound in combination with an oral rehydration solution (ORS).

3. The method according to claim 1, wherein the compound is present in a form selected from the group consisting of an oral rehydration solution (ORS), a nutritional composition, a dietary supplement, an infant formula and a follow on-formula.

4. The method according to claim 1, wherein a combination of the compound having formula (1) and the compound having formula (2) is administered.

5. The method according to claim 1, wherein a combination of the compound having formula (1) and the compound having formula (2) is administered, and wherein the combination is present in a composition that comprises the compound having formula (1) in an amount of at least 10% by weight of total butyrate moiety containing triglycerides in the composition, and the compound having formula (2) in an amount of at least 10% by weight of the total butyrate moiety containing triglycerides in the composition.

6. The method according to claim 1, wherein the compound having the formula (4) is present in a composition that comprises the compound having formula (4) as a main butyrate moiety containing triglyceride in the composition, wherein the compound of formula (4) provides at least 20%, by weight of total butyrate moiety containing triglycerides in the composition.

7. The method according to claim 1, wherein a combination of the compound having formula (1), the compound having formula (2), the compound having formula (3) and the compound having formula (4) is administered.

8. The method according to claim 1, wherein $R^1$, $R^2$, $R^3$, $R^4$, $R^5$ and/or $R^6$ is selected from the group consisting of oleic acid, palmitic acid, and linoleic acid.

9. The method according to claim 1, wherein each of $R^1$, $R^2$, $R^3$, $R^4$, $R^5$ and $R^6$ is oleic acid.

* * * * *